United States Patent [19]

Neidleman et al.

[11] 4,404,283
[45] Sep. 13, 1983

[54] LONG CHAIN WAX ESTERS AND METHOD OF MAKING SAME

[75] Inventors: Saul L. Neidleman, Oakland; John Geigert, Clayton, both of Calif.

[73] Assignee: Standard Oil Company (Ind.), Chicago, Ill.

[21] Appl. No.: 195,876

[22] Filed: Oct. 10, 1980

[51] Int. Cl.³ .................... C12P 7/64; C12R 1/265
[52] U.S. Cl. .................................. 435/134; 435/859
[58] Field of Search ............. 435/134, 863, 865, 923, 435/921, 872, 939, 929, 844

[56] References Cited

U.S. PATENT DOCUMENTS 3,169,099 2/1965 Davis ................................. 435/134
3,409,506 11/1968 Stevens et al. ................... 435/134
4,059,488 11/1977 Hachikubo et al. .............. 435/134

Primary Examiner—Hiram H. Bernstein
Attorney, Agent, or Firm—Marjorie D. Hunter; William T. McClain; William H. Magidson

[57] ABSTRACT

A method is described for the manufacture of wax esters from saturated hydrocarbons by the metabolic action of microorganisms. These wax esters contain either 0, 1 or 2 internally located carbon-carbon double bonds, with no more than 1 carbon-carbon double bond being in the fatty acid or the fatty alcohol segments. These wax esters are chemically similar to the wax esters of sperm whale oil and jojoba oil, and are useful as lubricants and lubricant additives, for example. They also are a ready source of industrially important mono-ene fatty acids and fatty alcohols, when saponified.

2 Claims, No Drawings

LONG CHAIN WAX ESTERS AND METHOD OF MAKING SAME

BACKGROUND OF THE INVENTION

There exists a need for a reliable synthetic mold release lubricant. The continuous casting of steel is considered as one of the major technological advances in the steel industry in recent years. In conventional steelmaking, up to 30% of the steel poured is lost in ingot trimming and mill scale; continuous casting cuts these losses down to 10% or less. Based on the use of 4–6 ounces of lubricant per ton, a substantial market for lubricants for continuous casting of steel is developing.

Without continuous and reliable lubrication of the mold walls, the steel-making process slows down or stops. U.S. Pat. No. 4,152,278 discloses lubricant compositions comprising wax esters of fatty acids and alcohols, particularly advantageous in the continuous casting of steel. These wax esters contain either 0, 1, 2, 3 or 4 internally located carbon-carbon double bonds, with no more than 2 isolated carbon-carbon double bonds being in the fatty acid or the fatty alcohol segments. The fatty acid and fatty alcohol segments are 14 to 17 carbons in length. These wax esters are derived from vegetable oil derivatives and involve the somewhat complicated chemical synthesis comprising reduction of the fatty acid to the fatty alcohol, which is then esterified with the fatty acid with rigorous removal of the water of esterification. Moreover, the compositions prepared are limited by the carbon chain length and the degree of carbon-carbon double bond unsaturation in the original vegetable oil derivative.

Also in the field of lubrication, there exists a need for synthetic, extreme pressure and antiwear lubricant additives. Additives prevent destructive metal-to-metal contact in lubrication at high pressure and/or temperature such as that found in certain gear elements in automotive vehicles and various industrial machines.

Sperm whale oil has been used extensively in these additives. This oil is comprised primarily of wax esters. These wax esters contain either 0, 1 or 2 internally located carbon-carbon double bonds, with no more than 1 carbon-carbon double bond being in the fatty acid or the fatty alcohol segments. The fatty acid and fatty alcohol segments are 15 to 18 carbons in length. Sperm whale oil has good lubricity, good load-bearing ability, and miscibility with the usual types of base oils. However, in 1970, the United States placed the sperm whale on the endangered species list and, in 1971, banned the import of its products.

Jojoba oil has the same properties as sperm whale oil. This oil obtained from the bean of the jojoba plant is pure wax ester. These wax esters contain 2 internally located carbon-carbon double bonds, with 1 carbon-carbon double bond in the fatty acid and the fatty alcohol segments. The fatty acid and fatty alcohol segments are 20–22 carbons in length. In laboratory testing, jojoba oil is comparable or superior to sperm whale oil (Miwa et al., JAOCS 56:765-770 (1979)) as a lubricant additive at high pressure and/or temperature.

However, this natural wax ester source requires 5 years from the date of planting of seedlings before an adequate amount of bean is born for commercialization (National Academy of Sciences, Committee on Jojoba Utilization (1975)). Moreover, the wax esters obtained are limited to 40 to 44 total carbon chain length and di-unsaturation.

The chemical properties which make the above wax esters useful as lubricants are:
1. A carbon chain length for the fatty acid and fatty alcohol segments of at least 14 carbons.
2. The presence of a carbon-carbon double bond in the fatty acid and/or the fatty alcohol segments.
3. The position of the unsaturation being internally, rather than terminally, located.

Microorganisms are a potential source of wax esters. Through metabolic action, wax esters can be produced from inexpensive, readily available hydrocarbons. For example, U.S. Pat. No. 3,409,506 describes the production of wax esters by *Micrococcus cerificans* (now referred to as Acinetobacter sp. HO1-N) from aliphatic hydrocarbon feedstocks.

Primary advantages of microbial production of wax esters are in the ability and flexibility in controlling the carbon chain length of the fatty acid and the fatty alcohol segments and the degree of unsaturation present. Thus, for example, if a $C_{16}$ hydrocarbon is employed as the feed, the principal wax ester will have a carbon chain length of 16 for the fatty acid and fatty alcohol segments. The primary disadvantage of previous reports on microbial production of wax esters is that saturated, not unsaturated, wax esters are formed. The presence of the carbon-carbon double bond in the fatty acid and/or the fatty alcohol segments in necessary to impart the desired lubrication properties. U.S. Pat. No. 3,409,506 discloses that *Micrococcus cerificans* produces only cetyl palmitate (saturated wax ester) from hexadecane. Stewart et al., J. Bact. 78:726-730 (1959) state that *Micrococcus cerificans* produces only octadecyl stearate (saturated wax ester) from octadecane. Makula et al., *J. Bact.* 121:250-258 (1975) claim that only 1 wax ester component (cetyl palmitate, saturated wax ester) is formed by Acinetobacter sp. HO1-N acting on hexadecane. Raymond et al., *Adv. Appl. Microbiol.* 14:93-121 (1971) and Krasilnikov et al., Mikrobiologiya 38:757-760 (1969) state the same finding (hexadecane yields cetyl palmitate only) for Nocardia species and Mycobacterium species, respectively. It has never been reported that microorganisms can produce wax esters containing carbon-carbon double bonds by metabolic action on saturated hydrocarbons. Saturated hydrocarbon feedstocks are expected to yield saturated wax esters according to present state of the art.

Attempts have been made to produce wax esters containing carbon-carbon double bonds by feedstocks other than saturated hydrocarbons. The metabolic action of Acinetobacter sp. HO1-N (Makula et al., *J. Bact.* 121:250-258 (1975)) and 3 species of Acinetobacter (Gallagher, *J. Gen. Microbiol.* 68:245-247 (1971)) on amino acid feed stocks yielded unsaturated wax esters. Fixter et al., *Biochem. Soc., Transl.* 4:504-505 (1976), reported that the metabolic action of Acinetobacter species on acetate or succinate feedstocks yielded wax esters containing $C_{14}$, $C_{16}$ and $C_{18}$ saturated and mono-unsaturated fatty acid and fatty alcohol segments. The high cost of these substrates relative to aliphatic hydrocarbon feeds is a disadvantage. The metabolic action of *Candida lipolytica* on olefinic feedstocks yielded unsaturated wax esters (Stewart et al., *Science* 132:1254 (1960)). The high cost of unsaturated hydrocarbon feeds relative to saturated ones is a disadvantage. Moreover, the carbon-carbon double bond is in the terminal position on the wax esters. The unsaturation needs to be internal, rather than terminal, to impart the much needed oxidative stability.

SUMMARY OF THE INVENTION

We have now surprisingly found that microorganisms can act on readily available and inexpensive saturated hydrocarbon feeds to produce lubricants and lubricant additives similar in chemical structure to the composition of sperm whale oil and jojoba oil, that is, wax esters comprised of long-chain fatty acids and fatty alcohols, having 0, 1 or 2 carbon-carbon double bonds, with no more than 1 carbon-carbon double bond being in the fatty acid or the fatty alcohol segments, and with the unsaturation being internally located along the carbon chains. This wax ester composition is characterized by the structural formula:

$$RCO_2R'$$

where R and R' are a radical selected from the group consisting of:

$$CH_3(CH_2)_aCH{=}CH(CH_2)_b{-} \quad (1)$$

where a = 5, 7 and a + b = 11–26;

$$CH_3(CH_2)_c{-} \quad (2)$$

where c = 14–29.
More particularly, the mixture of wax esters produced are predominantly of the formulas:

$$CH_3(CH_2)_wCH{=}CH(CH_2)_xCO_2(CH_2)_yCH{=}CH(CH_2)_zCH_3; \quad (1)$$

$$CH_3(CH_2)_wCH{=}CH(CH_2)_xCO_2(CH_2)_{y+z+2}CH_3; \quad (2)$$

$$CH_3(CH_2)_{w+x+2}CO_2(CH_2)_yCH{=}CH(CH_2)_zCH_3; \text{ and} \quad (3)$$

$$CH_3(CH_2)_{w+x+2}CO_2(CH_2)_{y+z+2}CH_3, \quad (4)$$

wherein w = 5, 7; w + x + 2 = 13–28; z = 5, 7; and y + z + 2 = 14–29.
For purposes herein, a saturated hydrocarbon is defined as a linear long-chain hydrocarbon not containing a carbon-carbon double bond, but which can contain functionalization such as hydroxyl and carboxyl groups.

The process of preparation comprises the steps of selectively fermenting a saturated hydrocarbon feed stock with a known microorganism and recovering the wax esters.

We have also found that the level of unsaturation in the produced wax ester mixture is controllable. The fermentation temperature and time, and the chain length of the hydrocarbon feed, contribute individually or in concert to this control.

In accordance with these findings, it is therefore an object of the present invention to prepare lubricant compositions, comprised of long-chain wax esters having carbon-carbon double bonds, to replace sperm whale oil.

Another object of the present invention is to prepare the wax ester compositions entirely from readily available and inexpensive saturated hydrocarbon feedstocks.

It is also an object of the present invention to control the level of unsaturation in the wax ester compositions.

Other objects and advantages of this invention will become readily apparent from the ensuing discussion.

DETAILED DESCRIPTION OF THE INVENTION

Microorganisms for use in the preparation of wax ester compositions of the invention include bacteria and fungi capable of assimilating saturated hydrocarbons and producing wax esters from them. Such microorganisms include *Mycobacterium ceriformans, Mycobacterium fortuitum, Mycobacterium rhodocrous, Candida lipolytica, Candida guilliermondii, Nocardia brasiliensis, Hormondendrum hordei, Rhizopus arrhizus, Fusarium lini, Corynebacterium paurometabolum* and *Corynebacterium diptheriae*. A preferred microorganism is Acinetobacter sp. HO1-N, also known as *Micrococcus cerificans*.

Suitable starting materials for use in the preparation of the wax ester compositions of the invention include $C_{15}$ through $C_{30}$ n-alkanes, n-alcohols and n-acids; petroleum hydrocarbon fractions in the $C_{15}$ through $C_{30}$ range.

The preferred hydrocarbon feed depends upon the wax ester composition desired. Preferred feeds for synthetic sperm whale oil are either $C_{16}$–$C_{18}$ n-alkanes or petroleum hydrocarbon fraction in the $C_{16}$–$C_{18}$ range. Preferred feeds for synthetic jojoba oil are either $C_{20}$–$C_{22}$ n-alkanes or petroleum hydrocarbon fraction in the $C_{20}$–$C_{22}$ range.

Generally, the wax ester production is conducted by aerobically cultivating the microorganism in an aqueous mineral salts solution to which the saturated hydrocarbon feed has been added. A preferred fermentation method and reactor for Acinetobacter sp. HO1-N is presented in U.S. Pat. No. 3,409,506, which is herein incorporated by reference.

Other fermentation approaches are familiar to those skilled in this art.

The degree of carbon-carbon double bond unsaturation in the produced wax esters is controlled by the fermentation conditions. Operating the fermentation at 19° C. results in a significant increase in the amount of di-unsaturated (mono-ene acid and mono-ene alcohol segments) wax ester component versus operation at 25° C. Operating the fermentation at 30° C. results in a significant increase in the amount of saturated wax ester component versus operation at 25° C. Operating the fermentation for 24 hours at a given temperature results in a significant increase in the amount of di-unsaturated (mono-ene acid and mono-ene alcohol segments) wax ester component versus operation for only 10 hours. This control over unsaturation has peviously been reported in the microbial production of a product other than wax ester:fatty acids (Gill, *J. Gen. Microbiol.* 104:31-36 (1978)).

The degree of carbon-carbon double bond unsaturation in the produced wax esters is also controlled by the chain length of the starting material. Using $C_{20}$ saturated hydrocarbon results in a significant increase in the amount of di-unsaturated (mono-ene acid and mono-ene alcohol segments) wax ester component versus using $C_{16}$ saturated hydrocarbon, at a given fermentation temperature and reaction time.

The resultant wax esters are recovered according to any conventional procedure. A preferred recovery method for fermentations of Acinetobacter sp. HO1-N is presented in U.S. Pat. No. 3,409,506, herein incorporated by reference.

Analysis of the wax ester compositions is accomplished by glass capillary gas chromatography, $(GC)^2$. A 25 meter OV-101 glass capillary column, operated at 40° C. to 325° C. at 10° C./minute temperature programming, is attached to a Finnigan 4021 GCMS. Wax ester samples are dissolved in carbon disulfide and 3μ/ml injected onto the column in the splitless mode. Detection is made possible by a flame ionization detector. (GC)$^2$ resolves the wax ester compositions by total carbon chain length and by degree of carbon-carbon double bond unsaturation (order of elution: di-ene, mono-ene, then saturated). It was the development of this powerful analytical tool that permitted the discovery of the invention to be made. Structure identification is made possible by operating the mass spectrometer (MS) at 70 eV electron impact ionization. The (GC)$^2$ MS analysis provides the total chain length, the chain length of the fatty acid segment, the chain length of the fatty alcohol segment, the presence and number of carbon-carbon double bonds in the fatty acid segment and the presence and number of carbon-carbon double bonds in the fatty alcohol segment of each wax ester component in the composition (Aasen et al, *Lipids* 6:502-507 (1970)). The position of the carbon-carbon double bond in the carbon chain is obtained by derivatizing the wax ester components (Duncan, *JAOCS* 51:534-536 (1974); Janssen, *Biomed. Mass Spectrom.* 5:439-443 (1978)) and then reanalyzing them by (GC)$^2$ MS.

These wax esters may be sulfurized according to any conventional procedure and used as synthetic sperm whale oil or synthetic jojoba oil. Also, they may be saponified according to any conventional procedure and the resulting mono-ene fatty acids and mono-ene fatty alcohols obtained. Such long-chain acids and alcohols have use as paint binders, surfactants and plasticizers (Pryde, *JAOCS* 56:849-854 (1979)).

The following examples are intended only to further illustrate the invention and are not intended to limit the scope of the invention which is defined by the claims.

EXAMPLE 1

Acinetobacter sp. HO1-N, ATCC No. 14987, was grown and maintained on the following agar-based medium:

| Component | Concentration (grams/liter) |
|---|---|
| Mueller Hinton Broth | 21 |
| Agar | 20 |

The organism was grown for 1 day at 25° C. The slants could be used immediately to inoculate seed cultures or could be stored for up to 30 days at 4° C. prior to use.

A seed stage of the microorganism was initiated by transferring the culture from the slant into aqueous, mineral salts medium prepared as follows:

| Component | Concentration (grams/liter) |
|---|---|
| $K_2HPO_4$ | 5.0 |
| $(NH_4)_2HPO_4$ | 10.0 |
| $CaCl_2.2H_2O$ | 0.1 |
| $FeSO_4.7H_2O$ | 0.04 |
| KCl | 1.0 |
| $MgSO_4$ | 0.1 |
| $MnSO_4.H_2O$ | 0.04 |
| $Na_2SO_4$ | 0.05 |

-continued

| Component | Concentration (grams/liter) |
|---|---|
| NaCl | 0.02 |

To this medium, 5 grams/liter of sodium acetate and 5 grams/liter sodium propionate were added as the carbon source.

The pH was adjusted to about 7.2, and 50 ml of the medium was introduced into a 250 ml glass Erlenmeyer flask and sterilized at 121° C. at 15 p.s.i. for 15 minutes.

The organism was shaken for 1 day at 25° C. at 200 r.p.m. Twenty-five ml of this seed stage was used to inoculate the reaction stage.

The reaction stage consisted of 200 ml of the above aqueous mineral salts medium in a 1 liter glass Erlenmeyer flask, sterilized at 121° C. at 15 p.s.i. for 15 minutes.

After cooling, n-hexadecane (400 mg) was aseptically added to the flask and the flask shaken for 2 hours to allow for saturation of the medium with the hydrocarbon feed. Then, 25 ml of an 18-hour vegetative inoculum of Acinetobacter sp. HO1-N was introduced into the flask. The reaction was run under shaking conditions (250 r.p.m.) at 25° C. for 24 hours.

After 24 hours, the flask contents were extracted with two 100 ml volumes of chloroform. Thereafter, the extract was dried down by heating at 80° C.

The extract residue was analyzed by thin layer chromatography using silica gel GF plates (E. Merck) and a solvent system consisting of hexane:chloroform (75:25). After development and drying, the plates were sprayed with alpha-cyclodextrin reagent spray (Supelco) and then exposed to iodine vapors in a closed tank. Lipid components appear as white spots on a purple-brown background. This TLC system cleanly resolves lipid components: $R_f$ 0.85 n-alkane; $R_f$ 0.55 wax ester; $R_f$ 0.20 triglyceride; $R_f$ 0.08 n-alcohol; $R_f$ 0.02 n-acid. The extract residue showed 2 spots. One spot had an $R_f$ of 0.85, which matched the $R_f$ for an alkane; the other spot had an $R_f$ of 0.55, which matched the $R_f$ of a wax ester.

Separation of residual starting n-alkane from biosynthesized wax ester was accomplished by transferring the extract residue to the head of a glass column (30 cm × 3 cm) packed with silica gel (E. Merck). Hexane solvent (150 ml) was passed through the column first to elute the residual starting alkane. Hexane:ethyl ether (90:10) solvent (150 ml) was then passed through the column to elute the produced wax esters. The solvent in this fraction was removed by heating at 50° C. The amount of wax ester isolated was 50 mg.

Analysis of the wax ester compositions was accomplished by glass capillary gas chromatography, (GC)$^2$. A 25 meter OV-101 glass capillary column, operated at 40° C. to 325° C. at 10° C./minute temperature programming, was attached to a Finnigan 4021 GCMS. Wax ester samples were dissolved in carbon disulfide and 3 microliter injected onto the column in the splitless mode. Detection was made possible by a flame ionization detector. Structure identification was made possible by operating the mass spectrometer (MS) at 70 eV electron impact ionization.

(GC)$^2$ analysis using flame ionization detection yielded 3 predominant wax ester peaks on the chromatogram: peak 1 had a retention time of 29.0 minutes, which corresponded to the retention time of authentic hexadecenyl hexadecenoate; peak 2 had a retention time of 29.6 minutes, which corresponded to the retention time of authentic hexadecenyl hexadecanoate; peak 3 had a retention time of 30.1 minutes, which corresponded to the retention time of authentic hexadecyl hexadecanoate (cetyl palmitate). A portion of the produced wax ester was subjected to hydrogenation under conditions known to reduce only carbon-carbon double bonds (Dees, *J. Clin. Microbiol.* 1:414-418 (1975)): 5 mg wax ester, 0.05 g of 5% platinum on charcoal in 2 ml of chloroform:methanol (3:1) were reacted in a pressure vessel pressurized to 50 p.s.i., at 25° C., for 5 hours. $(GC)^2$ analysis of the hydrogenated product yielded only 1 wax ester peak with a retention time of 30.1 minutes, coresponding to cetyl palmitate.

$(GC)^2$ MS analysis revealed the following about the 3 wax ester peaks. Peak 1 had a molecular weight of 476 and 2 diagnostic fragment mass ions of mass 222 and 236. This mass spectrum was identical to that of an authentic sample of hexadecenyl hexadecenoate. Peak 2 had a molecular weight of 478 and 4 diagnostic fragment mass ions of mass 222, 224, 236 and 257. This mass spectrum was identical to that of a mix of an authentic sample of hexadecenyl hexadecanoate and hexadecyl hexadecenoate. Peak 3 had a molecular weight of 480 and 2 diagnostic fragment mass ions of mass 224 and 257. This mass spectrum was identical to that of an authentic sample of cetyl palmitate.

These analyses confirmed the following structures for the wax esters produced:

| Peak 1 | $CH_3(CH_2)_wCH=CH(CH_2)_xCO_2(CH_2)_yCH=CH(CH_2)_zCH_3$ |
|---|---|
| Peak 2 | $CH_3(CH_2)_wCH=CH(CH_2)_xCO_2(CH_2)_{15}CH_3$ + $CH_3(CH_2)_{14}CO_2(CH_2)_yCH=CH(CH_2)_zCH_3$ |
| Peak 3 | $CH_3(CH_2)_{14}CO_2(CH_2)_{15}CH_3$ | where $w + x = 12$
$y + z = 13$

Determination of the position of the carbon-carbon double bond(s) in the wax esters was made by subjecting the product to ethanolysis, followed by oxidation and silylation. The wax ester (10 mg) was added to anhydrous ethanol (5 ml) plus anhydrous benzene (0.1 ml) in a 25 ml Erlenmeyer flask. Hydrogen chloride gas was slowly bubbled in for 2 hours while refluxing the flask contents. The solvent was then removed by heating at 70° C. Ethanolysis cleaves wax ester into fatty acid ethyl esters and free fatty alcohols.

$(GC)^2$ MS analysis of the ethanolysis products yielded 4 peaks on the chromatogram. Peak 1 had a retention time of 16.0 minutes, a molecular weight of 240 and a diagnostic fragment mass ion at mass 222. This elution time and mass spectrum were identical to that of an authentic sample of 1-hexadecenol:

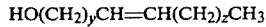
$HO(CH_2)_yCH=CH(CH_2)_zCH_3$ were $y+z=13$

Peak 2 had a retention time of 17.0 minutes, a molecular weight of 242 and a diagnostic fragment mass ion of mass 224. This elution time and mass spectrum were identical to that of an authentic sample of 1-hexadecanol:

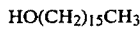
$HO(CH_2)_{15}CH_3$

Peak 3 had a retention time of 18.5 minutes, a molecular weight of 282 and 2 diagnostic fragment mass ions of 88 and 236. This elution time and mass spectrum were identical to that of an authentic sample of hexadecenoic acid ethyl ester:

$CH_3(CH_2)_wCH=CH(CH_2)_xCO_2CH_2CH_3$ where $w+x=12$

Peak 4 had a retention time of 20.0 minutes, a molecular weight of 284 and a diagnostic fragment mass ion of mass 88. This elution time and mass spectrum were identical to that of an authentic sample of hexadecanoic acid ethyl ester:

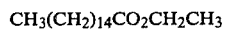
$CH_3(CH_2)_{14}CO_2CH_2CH_3$

The ethanolysis products were then subjected to oxidation and silylation. Oxidation with osmonium tetraoxide forms diols at the site of the carbon-carbon double bond. Silylation forms the silyl derivatives of the diols. In the mass spectrometer, the silyl derivatives fragment into diagnostic fragment mass ions, cleaving the bond between the carbons that contained the original carbon-carbon double bond.

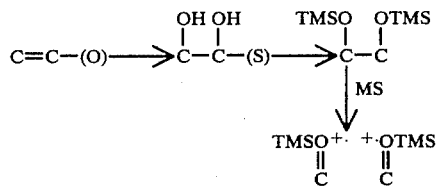

Into 2 ml of dioxane and 0.1 ml of pyridine, the ethanolysis products from the previous step were added. Osmonium tetraoxide (20 mg) was added. The resulting solution was kept at room temperature for 1 hour. The solvent was then evaporated off at 50° C. under vacuum and 5 ml of methanol added. Hydrogen sulfide gas was continuously bubbled through the solution for 3 minutes. The resulting black precipitate was removed by centrifuging and the supernatant was evaporated to dryness at 50° C. under vacuum. The residue was reacted for 30 minutes at 25° C. with 2 ml of Tri-Sil (Pierce Chemicals) to produce the silylated products. The solution was then evaporated to dryness at 40° C. under vacuum.

$(GC)^2$ MS analysis of the oxidized-silylated product yielded 4 peaks on the chromatogram. Peak 1 had a retention time of 20.0 minutes and showed the same mass spectrum as the unreacted hexadecanoic acid ethyl ester:

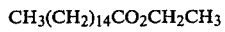
$CH_3(CH_2)_{14}CO_2CH_2CH_3$

Peak 2 had a retention time of 22.0 minutes and showed the same mass spectrum as an authentic sample of silylated 1-hexadecanol:

$TMSO(CH_2)_{15}CH_3$

Therefore, peaks 1 and 2 were due to ethanolysis products not containing carbon-carbon double bonds.

Peak 3 had a retention time of 26.3 minutes. Its mass spectrum showed an intense mass ion at mass 215 and a weak mass ion at mass 275, diagnostic of the following mono-ene fatty alcohol:

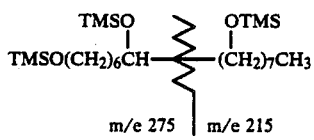

Peak 4 had a retention time of 29.5 minutes. Its mass spectrum showed 4 intense mass ions at mass 187, 215, 245 and 271, diagnostic of the following mono-ene fatty acid ethyl esters:

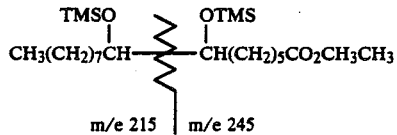

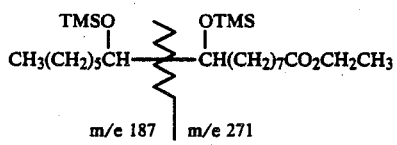

In summary, all of the data presented above clearly demonstrate the formation of the following wax esters by Acinetobacter sp. HO1-N acting upon n-hexadecane:

Structure

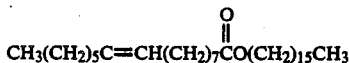

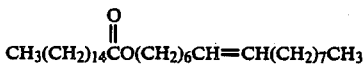

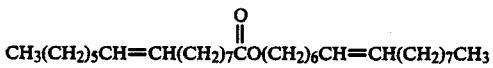

EXAMPLE 2

A series of reactions was performed in an identical manner as that performed in Example 1, substituting other n-alkanes for n-hexadecane.

The n-alkane hydrocarbons individually added were:
n-pentadecane—($C_{15}$)
n-heptadecane—($C_{17}$)
n-octadecane—($C_{18}$)
n-eicosane—($C_{20}$)
n-docosane—($C_{22}$)
n-tetracosane—($C_{24}$)

The analyses were performed as in Example 1 on the wax esters formed. These data clearly demonstrated the formation of the following wax esters by Acinetobacter sp. HO1-N acting upon the various n-alkanes:

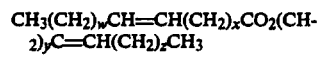

| n-Alkane Added | Predominant Wax Ester Components | | | |
|---|---|---|---|---|
| | w | w + x + 2 | z | y + z + 2 |
| $C_{16}$ | 5,7 | 14 | 7 | 15 |
| $C_{15}$ | 5,7 | 13 | 5,7 | 14 |
| $C_{17}$ | 5,7 | 14,15 | 5,7 | 15,16 |
| $C_{18}$ | 5,7 | 14,16 | 5,7 | 15,17 |
| $C_{19}$ | 5,7 | 15,16,17 | 5,7 | 17,18 |
| $C_{20}$ | 5,7 | 14,16,18 | 5,7 | 19 |
| $C_{22}$ | 5,7 | 16,18,20 | 5,7 | 21 |
| $C_{24}$[1] | 5,7 | 18 | 5,7 | 23 |

[1]Wax esters greater than 44 total carbons should have formed but they cannot be detected under the (GC)² conditions of operation.

EXAMPLE 3

A series of reactions was performed in an identical manner as that performed in Example 1, substituting n-alkane mixes for n-hexadecane.

The n-alkane hydrocarbon mixes added were:
n-hexadecane ($C_{16}$)+n-eicosane ($C_{20}$)
n-hexadecane ($C_{16}$)+n-docosane ($C_{22}$)
n-hexadecane ($C_{16}$)+n-tetracosane ($C_{24}$)
n-hexadecane ($C_{16}$)+n-octacosane ($C_{28}$)
n-eicosane ($C_{20}$)+n-docosane ($C_{22}$)
n-docosane ($C_{22}$)+n-tetracosane ($C_{24}$)
n-octadecane ($C_{18}$)+n-eicosane ($C_{20}$)+n-docosane ($C_{22}$)
n-eicosane ($C_{20}$)+n-docosane ($C_{22}$)+n-tetracosane ($C_{24}$)
n-octadecane ($C_{18}$)+n-eicosane ($C_{20}$)+n-docosane ($C_{22}$)+n-tetracosane ($C_{24}$)

The analyses were performed as in Example 1 on the wax esters formed. These data clearly demonstrated the formation of the following wax esters by Acinetobacter sp. HO1-N acting upon the various n-alkane mixes:

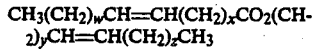

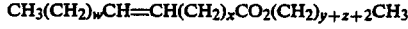

| n-Alkane Mix Added | Predominant Wax Ester Components | | | |
|---|---|---|---|---|
| | w | w + x + 2 | z | y + z + 2 |
| $C_{16} + C_{20}$ | 5,7 | 14,16,18 | 5,7 | 15,19 |
| $C_{16} + C_{22}$ | 5,7 | 14,16,18, 20 | 5,7 | 15,21 |
| $C_{16} + C_{24}$[1] | 5,7 | 14,18,20, 22 | 5,7 | 15,23 |
| $C_{16} + C_{28}$[1] | 5,7 | 14,22,24, 26 | 5,7 | 15,27 |
| $C_{20} + C_{22}$ | 5,7 | 14,16,18, 20 | 5,7 | 19,21 |
| $C_{22} + C_{24}$[1] | 5,7 | 16,18,20 | 5,7 | 21,23 |
| $C_{18} + C_{20} + C_{22}$ | 5,7 | 14,16,18, 20 | 5,7 | 17,19,21 |
| $C_{20} + C_{22} + C_{24}$[1] | 5,7 | 14,16,18, 22 | 5,7 | 19,21,23 |

| | Predominant Wax Ester Components | | | |
|---|---|---|---|---|
| n-Alkane Mix Added | w | w + x + 2 | z | y + z + 2 |
| $C_{18} + C_{20} + C_{22} + C_{24}$[1] | 5,7 | 14,16,18, 20,22 | 5,7 | 17,19, 21,23 |

[1] Wax esters greater than 44 total carbons should have formed but they cannot be detected under the $(GC)^2$ conditions of operation.

EXAMPLE 4

A reaction was performed in an identical manner as that performed in Example 1 substituting a petroleum hydrocarbon cut for n-hexadecane.

The petroleum hydrocarbon cut added was primary gas oil. This petroleum cut contained a range of n-alkanes, $C_{15}$ through $C_{27}$. This petroleum cut was enriched with n-hexadecane ($C_{16}$) to an approximate level of 25% of the weight of the total oil. This enrichment was done to facilitate ease of interpretation of the composition of the resulting wax esters. That is, the extra $C_{16}$ n-alkane favored the formation of 16 carbon chain length fatty acid segments, which were readily detected in the $(GC)^2$ MS analysis using the diagnostic mass ion of mass 257 for such segments. The analyses were performed as in Example 1 on the wax esters formed. These data clearly demonstrated the formation of the following wax esters by Acinetobacter sp. HO1-N acting upon a petroleum hydrocarbon cut containing added $C_{16}$ n-alkane:

$CH_3(CH_2)_w CH=CH(CH_2)_x CO_2(CH_2)_y CH=CH(CH_2)_z CH_3$ $CH_3(CH_2)_w CH=CH(CH_2)_x CO_2(CH_2)_{y+z+2} CH_3$ $CH_3(CH_2)_{w+x+2} CO_2(CH_2)_y CH=CH(CH_2)_z CH_3$ $CH_3(CH_2)_{w+x+2} CO_2(CH_2)_{y+z+2} CH_3$

| Predominant Wax Ester Components | | |
|---|---|---|
| w | w + x + 2 | y + z + 2 |
| 5,7 | 14 | 14–26 |

EXAMPLE 5

A series of reactions was performed in an identical manner as that performed in Example 1, substituting long-chain n-alcohols for n-hexadecane.

The n-alcohols individually added were:
n-1-hexadecanol—($C_{16}$)
n-1-octadecanol—($C_{18}$)
n-1-eicosanol—($C_{20}$)

The analyses were performed as in Example 1 on the wax esters formed. These data clearly demonstrated the formation of the following wax esters by Acinetobacter sp. HO1-N acting upon the various n-alcohols:

$CH_3(CH_2)_w CH=CH(CH_2)_x CO_2(CH_2)_y CH=CH(CH_2)_z CH_3$ $CH_3(CH_2)_w CH=CH(CH_2)_x CO_2(CH_2)_{y+z+2} CH_3$ $CH_3(CH_2)_{w+x+2} CO_2(CH_2)_y CH=CH(CH_2)_z CH_3$ $CH_3(CH_2)_{w+x+2} CO_2(CH_2)_{y+z+2} CH_3$

| | Predominant Wax Ester Components | | | |
|---|---|---|---|---|
| n-Alcohol Added | w | w + x + 2 | z | y + z + 2 |
| $C_{16}$ | 5,7 | 14 | 5,7 | 15 |
| $C_{18}$ | 5,7 | 14,16 | 5,7 | 17 |
| $C_{20}$ | 5,7 | 14,16,18 | 5,7 | 19 |

EXAMPLE 6

A series of reactions was performed in an identical manner as those performed in Example 1, substituting long-chain n-acids for n-hexadecane.

The n-acids individually added were:
n-hexadecanoic acid—($C_{16}$)
n-octadecanoic acid—($C_{18}$)
n-eicosanoic acid—($C_{20}$)

The analyses were performed as in Example 1 on the wax esters formed. These data clearly demonstrated the formation of the following wax esters by Acinetobacter sp. HO1-N acting upon the various n-acids:

$CH_3(CH_2)_w CH=CH(CH_2)_x CO_2(CH_2)_y CH=CH(CH_2)_z CH_3$ $CH_3(CH_2)_w CH=CH(CH_2)_x CO_2(CH_2)_{y+z+2} CH_3$ $CH_3(CH_2)_{w+x+2} CO_2(CH_2)_y CH=CH(CH_2)_z CH_3$ $CH_3(CH_2)_{w+x+2} CO_2(CH_2)_{y+z+2} CH_3$

| | Predominant Wax Ester Components | | | |
|---|---|---|---|---|
| n-Acid Added | w | w + x + 2 | z | y + z + 2 |
| $C_{16}$ | 5,7 | 14 | 5,7 | 15 |
| $C_{18}$ | 5,7 | 14,16 | 5,7 | 17 |
| $C_{20}$ | 5,7 | 14,16,18 | 5,7 | 19 |

EXAMPLE 7

A series of reactions was performed in an identical manner as that performed in Example 1, substituting mixed n-hydrocarbon and derivative feeds of 16, 18 and 20 carbon chain lengths for n-hexadecane.

The mixed hydrocarbons of a given carbon chain length added were:
n-alkane + n-alcohol
n-alkane + n-acid
n-alcohol + n-acid The analyses were performed as in Example 1 on the wax esters formed. These data clearly demonstrated the formation of the following wax esters by Acinetobacter sp. HO1-N acting upon the various mixed hydrocarbon and derivative feeds:

$CH_3(CH_2)_w CH=CH(CH_2)_x CO_2(CH_2)_y CH=CH(CH_2)_z CH_3$ $CH_3(CH_2)_w CH=CH(CH_2)_x CO_2(CH_2)_{y+z+2} CH_3$ $CH_3(CH_2)_{w+x+2} CO_2(CH_2)_y CH=CH(CH_2)_z CH_3$ $CH_3(CH_2)_{w+x+2} CO_2(CH_2)_{y+z+2} CH_3$

| Carbon Chain Length of Added Hydrocarbon Mix | | Predominant Wax Ester Components | | | |
|---|---|---|---|---|---|
| | | w | w + x + 2 | z | y + z + 2 |
| $C_{16}$ | alkane + | | | | |

-continued

| Carbon Chain Length of Added Hydrocarbon | Mix | Predominant Wax Ester Components | | | |
|---|---|---|---|---|---|
| | | w | w + x + 2 | z | y + z + 2 |
| $C_{18}$ | alcohol<br>alkane + acid<br>alcohol + acid | 5,7 | 14 | 5,7 | 15 |
| | alkane + alcohol<br>alkane + acid<br>alcohol + acid | 5,7 | 14,16 | 5,7 | 15,17 |
| $C_{20}$ | alkane + alcohol<br>alkane + acid<br>alcohol + acid | 5,7 | 14,16<br>18 | 5,7 | 19 |

EXAMPLE 8

This example demonstrates the control of wax ester unsaturation as a function of substrate carbon chain length.

A series of reactions was performed in an identical manner as that performed in Example 1, using hexadecane ($C_{16}$), octadecane ($C_{18}$) and eicosane ($C_{20}$).

The $(GC)^2$ analyses were performed as in Example 1 on the wax esters formed. These data clearly demonstrated the control of unsaturation as a function of substrate carbon chain length:

| n-Alkane Feed | Total Wax Esters | | |
|---|---|---|---|
| | Di-Ene Fraction | Mono-Ene Fraction | Saturated Fraction |
| $C_{16}$ | 5% | 15% | 80% |
| $C_{18}$ | 30% | 40% | 30% |
| $C_{20}$ | 60% | 30% | 10% |

EXAMPLE 9

This example demonstrates the control of wax ester unsaturation as a function of reaction temperature.

A series of reactions was performed in an identical manner as that performed in Example 1 using n-hexadecane ($C_{16}$) and n-eicosane ($C_{20}$) and running the reactions at 15° C., 21° C., 25° C. and 32° C.

The $(GC)^2$ analyses were performed as in Example 1 on the wax esters formed. These data clearly demonstrated the control of unsaturation as a function of reaction temperature:

| n-Alkane Feed | Reaction Temperature | Total Wax Esters | | |
|---|---|---|---|---|
| | | Di-Ene Fraction | Mono-Ene Fraction | Saturated Fraction |
| $C_{16}$ | 15° C. | 40% | 30% | 30% |
| | 21° C. | 30% | 30% | 40% |
| | 25° C. | 5% | 15% | 80% |
| | 32° C. | 2% | 8% | 90% |
| $C_{20}$ | 15° C. | 80% | 15% | 5% |
| | 21° C. | 72% | 20% | 8% |
| | 25° C. | 60% | 30% | 10% |
| | 32° C. | 20% | 30% | 50% |

EXAMPLE 10

This example demonstrates the control of unsaturation as a function of reaction time.

A reaction was performed in an identical manner as that performed in Example 1, substituting n-eicosane ($C_{20}$) for n-hexadecane. The reaction was sampled at several time points.

The $(GC)^2$ analyses were performed as in Example 1 on the wax esters formed. These data clearly demonstrated the control of unsaturation as a function of reaction time:

| Reaction Time | Total Wax Esters | | |
|---|---|---|---|
| | Di-Ene Fraction | Mono-Ene Fraction | Saturated Fraction |
| 4 hours | 20% | 60% | 20% |
| 8 | 30% | 55% | 15% |
| 12 | 45% | 45% | 10% |
| 24 | 60% | 30% | 10% |

EXAMPLE 11

*Corynebacterium paurometabolum*, ATCC No. 15530, was grown and maintained on the following agar-based medium:

| Component | Concentration (grams/liter) |
|---|---|
| Mueller Hinton Broth | 21 |
| Agar | 20 |

The organism was grown for 1 day at 30° C. The slants could be used immediately or could be stored up to 5 days at 4° C. prior to use.

A seed stage of the microorganism was initiated by transferring the culture from the slant into aqueous, mineral salts medium prepared as follows:

| Component | Concentration (grams/liter) |
|---|---|
| $K_2HPO_4$ | 5.0 |
| $(NH_4)_2HPO_4$ | 10.0 |
| $CaCl_2.2H_2O$ | 0.25 |
| $FeSO_4.7H_2O$ | 0.04 |
| KCl | 1.0 |
| $MgSO_4$ | 0.25 |
| $MnSO_4.H_2O$ | 0.04 |
| $Na_2SO_4$ | 0.50 |
| NaCl | 0.02 |

The medium (100 ml) was dispensed into a 500 ml wide-necked Erlenmeyer flask with double "milk filter" closure and sterilized by autoclaving. To this medium, n-hexadecane (0.1 ml) was added aseptically as the carbon source.

The culture was shaken for 3 days at 30° C. at 250 r.p.m.

The seed culture was centrifuged at 13,000 r.p.m. for 15 minutes and the cell pellet was washed once using 0.1 M potassium phosphate buffer (pH 7.0).

The cell pellet was resuspended into 25 ml of sterilized fermentation medium which was prepared as follows:

| Component | Concentration (grams/liter) |
| --- | --- |
| K$_2$HPO$_4$ | 5.0 |
| (NH$_4$)$_2$HPO$_4$ | 10.0 |
| CaCl$_2$.2H$_2$O | 0.1 |
| FeSO$_4$.7H$_2$O | 0.04 |
| KCl | 1.0 |
| MgSO$_4$ | 0.1 |
| MnSO$_4$.H$_2$O | 0.04 |
| Na$_2$SO$_4$ | 0.5 |
| NaCl | 0.02 |

(pH was adjusted with H$_2$SO$_4$ to 7.25 before autoclaving)

The cell pellet and fermentation medium were dispensed into a sterile 125 ml Erlenmeyer flask. n-hexadecane (20 microliter) was aseptically added to the flask.

The fermentation flask was incubated at 25° C. at 250 r.p.m. for 24 hours.

The analysis was performed as in Example 1 on the wax esters formed. These data clearly demonstrated the formation of the following wax esters by *Corynebacterium paurometabolum* acting upon n-hexadecane:

Structure

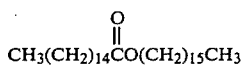

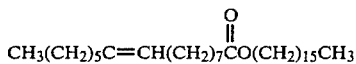

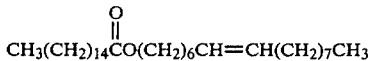

EXAMPLE 12

*Mycobacterium fortuitum*, NRLB No. 8119, Cetus No. 5099, was shaken in Mueller Hinton Broth at 30° C. at 250 r.p.m. for 24 hours.

A seed stage of the microorganism was initiated by transferring 1 ml of the culture into 200 ml of aqueous material salts medium prepared as follows:

| Component | Concentration (grams/liter) |
| --- | --- |
| K$_2$HPO$_4$ | 5.0 |
| (NH$_4$)$_2$HPO$_4$ | 10.0 |
| CaCl$_2$.2H$_2$O | 0.25 |
| FeSO$_4$.7H$_2$O | 0.04 |
| KCl | 1.0 |
| MgSO$_4$ | 0.25 |
| MnSO$_4$.H$_2$O | 0.04 |
| Na$_2$SO$_4$ | 0.5 |
| NaCl | 0.02 |

The aqueous salts medium (200 ml) was dispensed into a 500 ml Erlenmeyer flask and sterilized by autoclaving. n-hexadecane (0.2 ml) was added to the seed flask.

The culture was shaken for 3 days at 30° C. at 250 r.p.m.

The seed culture was centrifuged for 15 minutes at 13,000 r.p.m. followed by one washing of the cell pellet with 0.1 M potassium phosphate buffer (pH 7.0)

The culture pellet was resuspended into 25 ml of a mineral salts medium which was prepared as follows:

| Component | Concentration (grams/liter) |
| --- | --- |
| K$_2$HPO$_4$ | 5.0 |
| (NH$_4$)$_2$HPO$_4$ | 10.0 |
| CaCl$_2$.2H$_2$O | 0.1 |
| FeSO$_4$.7H$_2$O | 0.04 |
| KCl | 1.0 |
| MgSO$_4$ | 0.1 |
| MnSO$_4$.H$_2$O | 0.04 |
| Na$_2$SO$_4$ | 0.5 |
| NaCl | 0.02 |

(pH was adjusted with H$_2$SO$_4$ to 7.25 before autoclaving)

The cell pellet and fermentation medium were dispensed into a sterile 125 ml Erlenmeyer flask. n-hexadecane (20 microliter) was aseptically added to the flask.

The fermentation flask was incubated at 25° C. at 250 r.p.m. for 24 hours.

The analysis was performed as in Example 1 on the wax esters formed. These data clearly demonstrated the formation of the following wax esters by *Mycobacterium fortuitum* acting upon n-hexadecane:

Structure

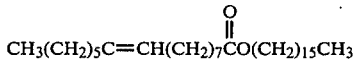

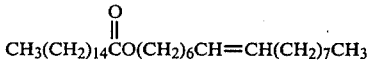

EXAMPLE 13

The growth conditions, seed stage and fermentation stage used in Example 12 were followed here, using *Mycobacterium rhodocrous*, ATCC No. 19067.

The analysis was performed as in Example 1 on the wax esters formed. The wax esters formed by *Mycobacterium fortuitum* acting upon n-hexadecane in Example 12 were also formed by *Mycobacterium rhodocrous*.

We claim:
1. A process for the production of wax esters comprising at least 50% by weight unsaturated wax esters comprising aerobically cultivating a microorganism comprising Acinetobacter in an aqueous mineral salts solution on a saturated hydrocarbon feed comprising $C_{16}$ n-alkanes at a temperature within the range of about 15° C. to about 21° C.

2. A process for the production of wax esters comprising at least 50% by weight unsaturated wax esters comprising aerobically cultivating a microorganism comprising Acinetobacter in an aqueous mineral salts solution on a saturated hydrocarbon feed comprising $C_{20}$ n-alkanes at a temperature of less than about 32° C.

* * * * *